United States Patent
Taguchi et al.

(10) Patent No.: US 11,975,113 B2
(45) Date of Patent: May 7, 2024

(54) WOUND DRESSING CONTAINING CROSSLINKED GELATIN DERIVATIVE PARTICLES

(71) Applicant: NATIONAL INSTITUTE FOR MATERIALS SCIENCE, Tsukuba (JP)

(72) Inventors: Tetsushi Taguchi, Tsukuba (JP); Akihiro Nishiguchi, Tsukuba (JP)

(73) Assignee: NATIONAL INSTITUTE FOR MATERIALS SCIENCE, Tsukuba (JP)

(*) Notice: Subject to any disclaimer, the term of this patent is extended or adjusted under 35 U.S.C. 154(b) by 0 days.

(21) Appl. No.: 16/642,887

(22) PCT Filed: Aug. 31, 2018

(86) PCT No.: PCT/JP2018/032503
§ 371 (c)(1),
(2) Date: Feb. 27, 2020

(87) PCT Pub. No.: WO2019/045081
PCT Pub. Date: Mar. 7, 2019

(65) Prior Publication Data
US 2020/0206382 A1    Jul. 2, 2020

(30) Foreign Application Priority Data

Sep. 4, 2017 (JP) ................... 2017-169127
Mar. 23, 2018 (JP) ................... 2018-056417

(51) Int. Cl.
*A61L 15/32* (2006.01)
*A61F 13/02* (2024.01)
*A61L 31/04* (2006.01)

(52) U.S. Cl.
CPC .............. *A61L 15/32* (2013.01); *A61F 13/02* (2013.01); *A61L 31/045* (2013.01)

(58) Field of Classification Search
CPC .......... A61L 15/32; A61L 31/045; A61F 13/02
See application file for complete search history.

(56) References Cited

U.S. PATENT DOCUMENTS

2011/0125089 A1* 5/2011 Senderoff .......... A61K 38/4833
604/82
2019/0336642 A1* 11/2019 Taguchi ............... A61L 24/104

FOREIGN PATENT DOCUMENTS

| JP | 2003-062057 A | 3/2003 |
| JP | 2010-083788 A | 4/2010 |

(Continued)

OTHER PUBLICATIONS

BeMatrix® Product Sheet, Nitta Gelatin Inc., retrieved online on Mar. 7, 2024, <URL: https://www.nitta-gelatin.co.jp/en/Products/biomedical/bematrix.html>. (Year: 2024).*

(Continued)

*Primary Examiner* — Michael B. Pallay
(74) *Attorney, Agent, or Firm* — Liang Legal Group, PLLC

(57) ABSTRACT

A wound dressing material includes a particle having a crosslinked gelatin derivative, the gelatin derivative having the structure represented by the following formula (1):

$$\text{GltnNH—CHR}^1\text{R}^2 \qquad (1)$$

wherein "Gltn" represents a gelatin residue, $R^1$ represents an alkyl group having 1-17 carbon atoms, and $R^2$ represents a hydrogen atom or an alkyl group having 1-17 carbon atoms, and the particle having a particle size ranging from 1 to 1,000 μm.

10 Claims, 9 Drawing Sheets

(56) References Cited

FOREIGN PATENT DOCUMENTS

| JP | 2011-025013 A | 2/2011 | | |
|---|---|---|---|---|
| JP | P5995128 B | 9/2016 | | |
| WO | WO-2017126390 A1 * | 7/2017 | ........... | A61L 24/043 |
| WO | 2017126390 A1 | 7/2018 | | |

OTHER PUBLICATIONS

Ryo Mazuta et al., "Enhanced Sealing by Hydrophobic Modification of Alaska Pollock-Derived Gelatin-Based Surgical Sealants for the Treatment of Pulmonary Air Leaks," Macromol. Biosci., Apr. 2017, 17(4): DOI: 10.1002/mabi.201600349, Wiley & Sons, Inc., Hoboken, NJ 07030-5774 U.S.A.

Akihiro Nishiguchi et al., "Development of spray-type wound dressing made of hydrophobized gelatin particles," Polymer Reprints, Japan, May 23-25, 2018, Annual Conference, 67(1): 1H12, Polymer Society of Japan, Tokyo, Japan.

Katsuya Kawai et al., "Accelerated tissue regeneration through incorporation of basic fibroblast growth factor—Impregnated gelatin microspheres into artificial dermis," Biomaterials 21 (2000) 489-499, Elsevier, Amsterdam, Netherland.

\* cited by examiner

Contact angle of original and derivatized gelatin particles

FIG. 10

Influences of particle concentration on cell survival rate

FIG. 11

Growth behaviors of cells on a film made of the particles
(*P<0.05, **P<0.01 (relative to ORG), n=4)

WOUND DRESSING CONTAINING CROSSLINKED GELATIN DERIVATIVE PARTICLES

TECHNICAL FIELD

The present invention relates to a wound dressing material, specifically to a wound dressing material comprising a particle comprising crosslinked gelatin derivative.

BACKGROUND OF THE INVENTION

A wound dressing material is defined in the Japanese Pharmaceutical Affairs Act, medical instrument classification, as follows: "wound dressing or protecting material: topically administered wound dressing or protecting material made of hydrophilic polymer used to absorb exudate, suppress breeding or loss of body fluid, and protect wound from scratch, friction, drying, or contamination." Examples of wound dressing material include gauze, polyurethane foam, and hydrogel, all of which are in the form of fabric.

The wound dressing material has begun to be used in Endoscopic Submucosal Dissection (ESD), which is a method of treating an early stage cancer such as the one in the stomach or the large intestine. Lining of the stomach or the large intestine comprises a mucosa, a submucosa and muscularis. Malignant tumors develop in the mucosa, which is the most inner layer. In ESD, the mucosa and the submucosa are peeled with gastroscope or colonoscope from the digestive tract lumen, whereby a lesion is dissected en-block. The remaining tissues after the dissection, if left as it is, contracts and adheres, causing deuteropathy such as digestive tract obstruction. To prevent this, the tissues are covered with a biodegradable wound dressing material.

A wound dressing material for ESD is required to have a shape conformity, that is, flexibility to conform to the shape of a wound, and biodegradability. Currently, polyglycolic acid nonwoven fabric (NEOVEIL (registered trademark), Gunze Ltd.) is used. The polyglycolic acid nonwoven fabric has an excellent biodegradability, but it has no adhesiveness to the tissues, so that the fabric should be fixed by covering it with a fibrin adhesive. The fibrin adhesive, however, is expensive and a blood product and thus is not free of the risk of contamination. In addition, the nonwoven fabric is difficult to expand on an application site and lacks the shape conformity for a site having a complicated shape. Further, polyglycolic acid oligomer, which is a biodegraded product, could cause the tissues inflammation.

Gelatin is used for various medical applications because of its excellent biocompatibility and biodegradability. Particulate drugs thereof are known such as an embolic agent for transarterial embolization treatment (Patent document 1), and a sustained release carrier (Non-Patent document 1). A chemically modified gelatin has been developed for medical use. For example, a tissue adhesive having a high adhesiveness to wet tissues is known wherein a gelatin has hydrophobic groups bonded thereto via imino group (Patent document 2).

REFERENCED DOCUMENTS

Patent Document

[Patent Document1] Japanese Patent Application Laid-Open No. 2010-83788
[Patent Document2] Japanese Patent No. 5995128

Non-Patent Document

[Non-Patent Document 1] Biomaterials, Vol. 21, pp 489-499, 2000

SUMMARY OF THE INVENTION

Problems to be Solved by the Invention

The present invention is to provide a wound dressing material which can be applied to conform to the shape of a wound, has a high adhesiveness to wet tissues and is biodegradable.

Means to Solve the Problems

Thus, the present invention is as follows:

A wound dressing material comprising a particle comprising a crosslinked gelatin derivative, the gelatin derivative comprising the structure represented by the following formula (1):

$$\text{GltnNH—CHR}^1\text{R}^2 \tag{1}$$

wherein "Gltn" represents a gelatin residue, $R^1$ represents an alkyl group having 1-17 carbon atoms, and $R^2$ represents a hydrogen atom or an alkyl group having 1-17 carbon atoms, and the particle having a particle size ranging from 1 to 1,000 μm.

Effects of the Invention

The aforesaid wound dressing material comprises a particle having a size of the order of μm, and can be applied by spraying to the shape of wound even having a complicated shape. The particle has an alkyl group to be highly adhesive even to the wet tissues. Further, the particle can be prepared without using a dispersion medium or a crosslinking agent to be applicable to the tissues without worrying about adverse effects caused by residues or decomposition products thereof.

DETAILED DESCRIPTION OF THE INVENTION

<Gelatin Derivative>

Figure 4:
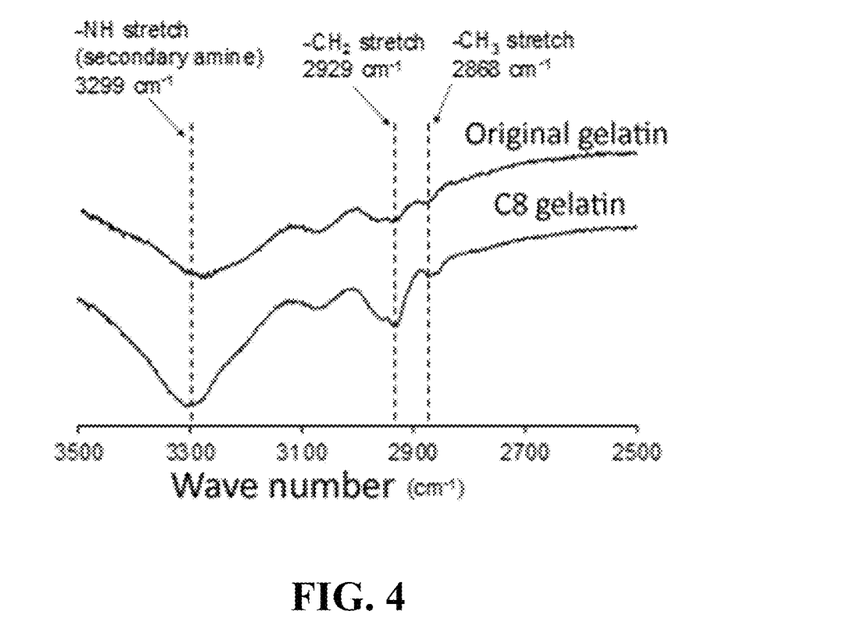
FIG. 4 shows a FT-IR spectrum of the gelatin derivative from 2,500 to 3,500 cm$^{-1}$.

In the present invention, the gelatin derivative comprises the structure represented by the following formula (1):

$$GltnNH—CHR^1R^2 \quad (1)$$

wherein "Gltn" represents a gelatin residue, $R^1$ represents an alkyl group having 1-17 carbon atoms, and $R^2$ represents a hydrogen atom or an alkyl group having 1-17 carbon atoms. N mainly originates from ε-amino group of lysine (Lys) in the gelatin. Preferably, $R^2$ is a hydrogen atom. The NH structure in the formula (1) can be identified by, for example, an absorption band around 3300 cm$^{-1}$ in FT-IR spectrum. FIG. 4 shows a FT-IR spectrum of the gelatin derivative of Example 7.

When $R^2$ is the alkyl group having 1 to 17 carbon atoms, it may be the same as or different from $R^1$. The alkyl group may be branched. Examples of the alkyl group include methyl group, ethyl group, propyl group, butyl group, hexyl group, octyl group (or caprylic group), nonyl group (or pelargonyl group), decyl group, dodecyl group (or lauryl group), tetradecyl group (or myristyl group). Preferably, $R^1$ is an alkyl group having 1 to 11 carbon atoms, preferably a linear alkyl group having 1 to 9 carbon atoms, and $R^2$ is a hydrogen atom.

A ratio of derivatization in the gelatin derivative is defined as a molar % of the imino group to which the alkyl group bonded relative to the amino group in the original gelatin, and ranges from 20 to 80 mol %, preferably from 30 to 70 mol %. In other words, a molar ratio of imino group/amino group in the obtained gelatin derivative ranges from 20/80 to 80/20, preferably from 30/70 to 70/30. The ratio of derivatization can be determined by quantifying amino group of an original gelatin and that of the gelatin having an alkyl group bonded thereto by titration with 2, 4, 6-trinitrobenzene sulfonic acid (TNBS method), or by quantitative identification of the alkyl group with NMR or the like.

The original gelatin may be of natural origin, synthesized, fermented, or genetically engineered gelatin. Preferably, a gelatin of animal origin such as porcine or bovine gelatin and a gelatin of fish origin such as Alaska pollock gelatin is used. The gelatin may be an acid-treated gelatin, an alkali-treated gelatin or genetically engineered gelatin, among which the alkali-treated gelatin is preferred, and a low endotoxin gelatin is more preferred. The gelatin preferably has a weight average molecular weight (Mw) of from 30,000 to 150,000, more preferably from 50,000 to 120,000. The molecular weight can be determined by gel permeation chromatography (GPC) according to a conventional procedure.

<Particle>

Figure 1:
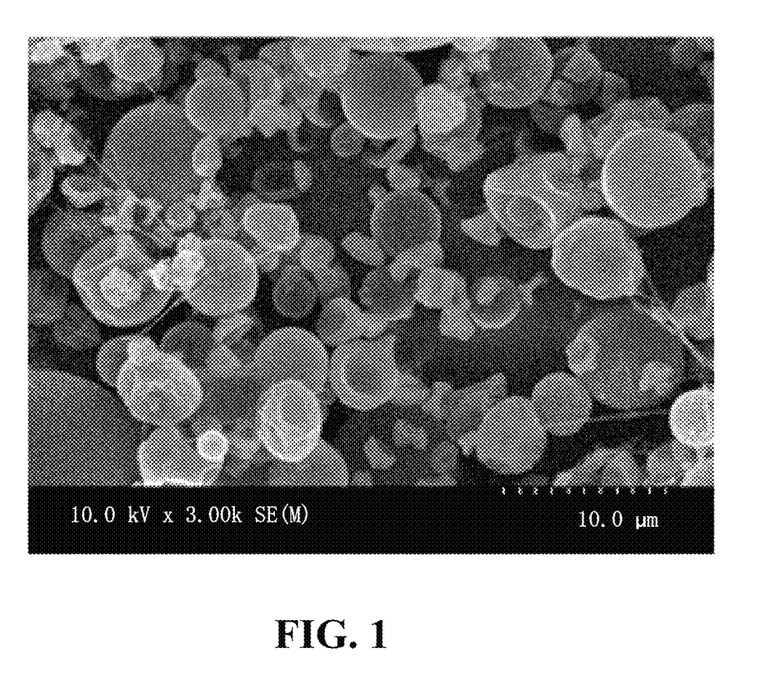
FIG. 1 shows a scanning electron microscope (SEM) image of the gelatin derivative particles.

FIG. 1 shows a Scanning Electron Microscope (SEM) image of exemplary particles of the present invention (Example 7). It can be seen that the particles are substantially spherical. A particle size thereof is in the order of micrometer, that is, ranges from 1 to 1,000 μm, mainly from 1 to 50 μm, with a mode diameter ranging from 10 to 20 μm. According to application site and application means, particles of a predetermined range of particle size can be selected by screening or the like. From the viewpoints of delivery and handling properties, the particle size preferably ranges from 1 to 200 μm, more preferably from 1 to 50 μm. In the present invention, the particle size was determined by SEM image analysis, but other method, for example, laser diffraction method or the like can be also used.

The particle can be prepared by spray drying a solution of the gelatin derivative or by pulverizing the gelatin derivative in solid state obtained by drying the solution, followed by thermally crosslinking. The spray drying is preferred. The method described in the aforesaid non-patent document 1 may be used wherein an aqueous solution of gelatin is dropped in an olive oil to form a gel in the form of oil-in-water emulsion and particles thus obtained are introduced in an aqueous solution of glutaraldehyde to be chemically crosslinked. However, the method of spray drying is preferred because no dispersion medium or crosslinking agent is used, so that there are no concerns of toxicity caused by residues or decomposition product thereof, no need of cleaning the dispersion medium off, and no concerns of aggregation of particles in drying process after cleaning process.

Figure 6:
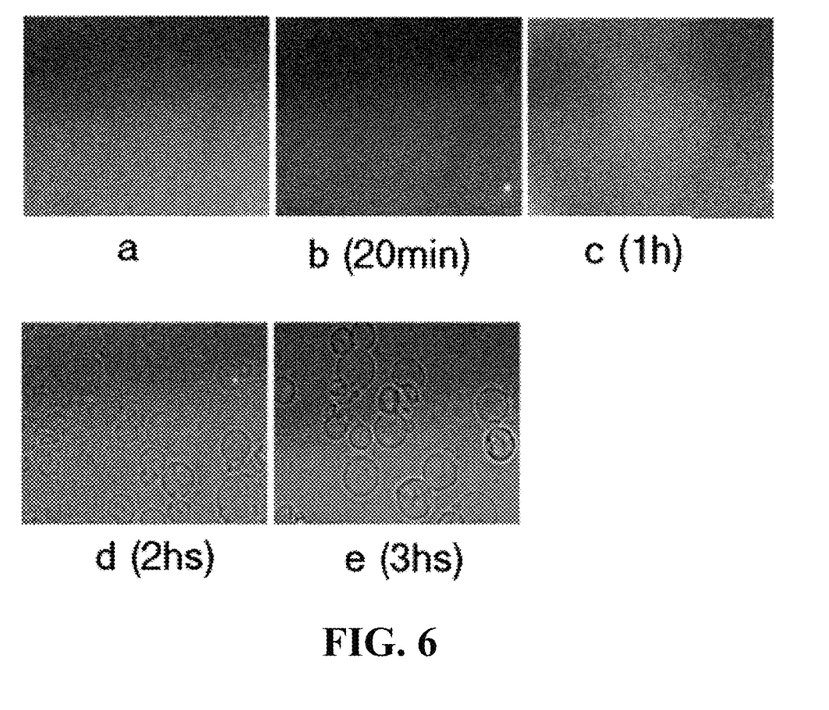
FIG. 6 shows phase-contrast micrographs of particles dispersed in water immediately after heat treatment for a period of time varied from 20 minutes to 3 hours.

The crosslinking of the gelatin derivative can be confirmed by observing visually or under phase-contrast microscope that particles do not dissolve in water when dispersed in water. FIGS. 6a to 6e show phase-contrast micrographs of particles dispersed in water immediately after heat treating particles prepared by spray drying (Example 7) for a period of time varied from 20 minutes to 3 hours at 150° C. and at a reduced pressure (<10 Pa) in a vacuum dryer. Particles without heat treatment (FIG. 6a), and those with 20-minute heat treatment (FIG. 6b) were dissolved in water; a part of those with 1-hour heat treatment (FIG. 6c) were found to be undissolved; many of those with 2-hour heat treatment (FIG. 6d) were found undissolved; and a little more of those with 3-hour heat treatment than those with 2-hour treatment (FIG. 6e) were undissolved.

Figure 7:
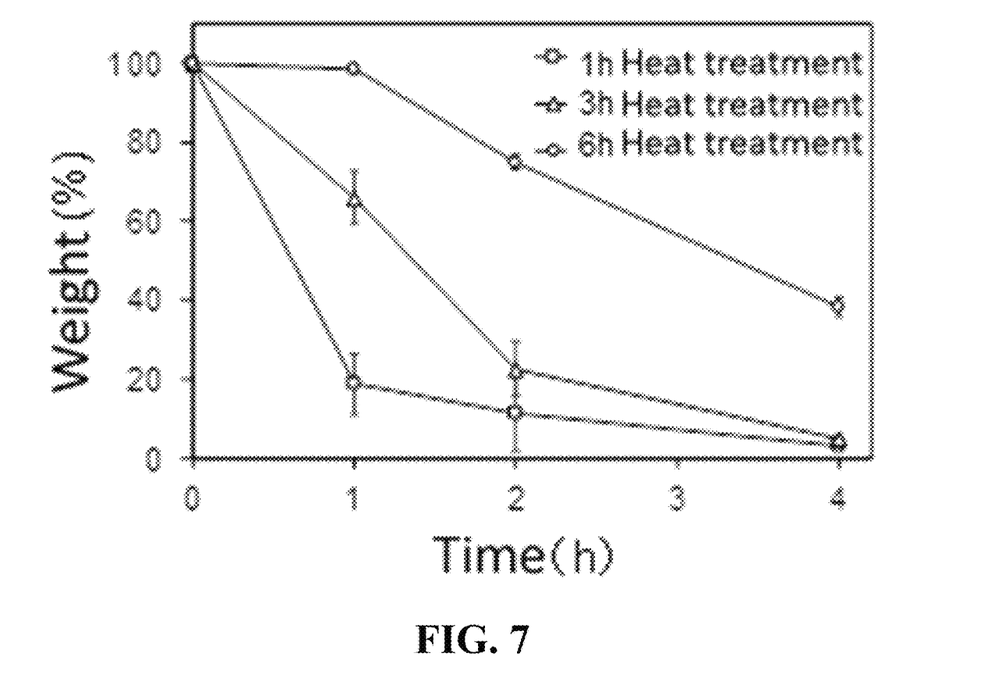
FIG. 7 is a graph showing a dissolving property in physiological saline of particles versus heat treatment time examined in an accelerated test in the presence of collagenase.

Dissolving property in the body fluid of the above particles with 1-hour, 3-hour, or 6-hour heat treatment was examined by an accelerated test in the presence of collagenase. Particles in an amount of 20 mg were dispersed in a solution of 5 μg/mL collagenase in PBS (pH=7.4) and, after 1, 2, or 4 hours, undissolved particles were collected by centrifugation and weighed after drying. The results are shown in FIG. 7. As shown in the graph, 3-hour heat treatment enables particles to show required initial absorption of the body fluid without being dissolved in the body fluid when applied as a wound dressing material. A time for dissolution increased with increased time of heat treatment, which indicates that dissolving property in the body fluid can be controlled by the time of heat treatment.

Figure 8:
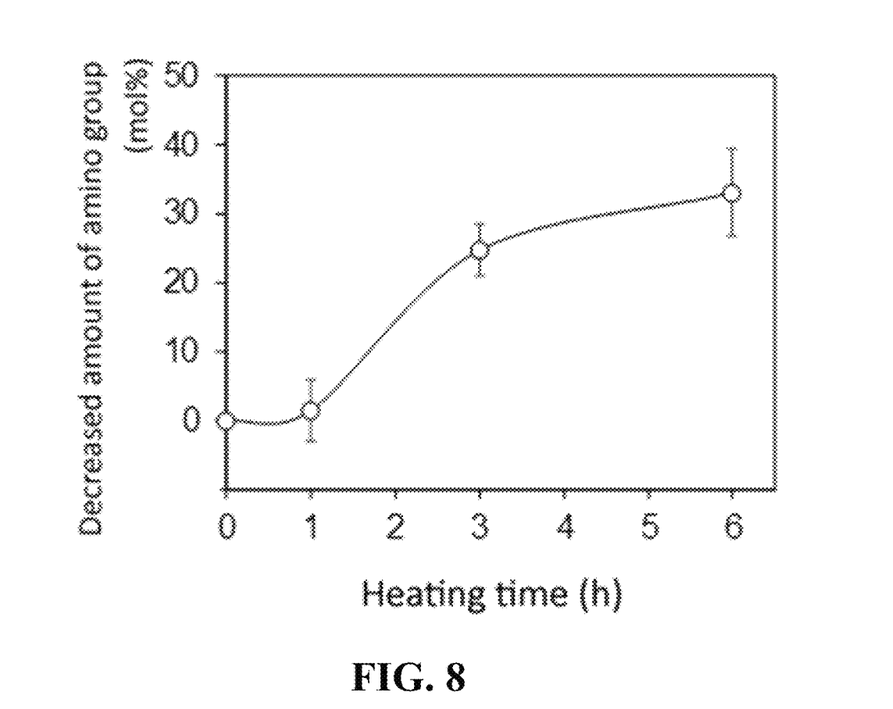
FIG. 8 is a graph showing amounts of amino groups which were consumed by heat treating at 150° C. spray dried particles obtained from an original gelatin and plotted versus heat treatment time.

A degree of crosslinking cannot be limited to a specific range because 100% of crosslinking, which is defined as a state where all the amino groups have reacted, varies according to the number of amino groups that can be involved in the crosslinking reaction depending on the degree of derivatization. FIG. 8 shows a graph of amounts of amino group consumed by the crosslinking plotted versus heat treatment time, which amounts were determined by measuring an amount of remaining amino groups by TNBS method of the particles prepared by spray drying an original gelatin followed by heat treatment at 150° C. As is found from the figure, the crosslinking rapidly advanced at 150° C. in the first 3 hours, and then gradually slowed to reach a plateau in 6 hours where about 40% of crosslinkable amino groups had been consumed. In a gelatin derivative, it was speculated that less amino groups remaining without derivatized lead to a less reactivity, so that 3-hour heat treatment would result in a plateau where 10 to 30% of crosslinkable amino group have been consumed. However, for the particles of Example 7 with derivatization ratio as high as 75%, 3-hour heat treatment showed satisfactory resistance to dissolution for the use as wound dressing material, which is considered to be attributed to the presence of the alkyl group.

<Additives>

The wound dressing material of the present invention may comprise various additives in such an amount that they do not adversely affect the objects of the present invention. Examples of the additives include colorants, and preservatives. It may comprise various drugs, for example, anti-thrombotic drugs, antibiotics, and various growth factors. The additives or drugs may be supported on or bonded to the particles.

<Method of Preparing the Wound Dressing Material>

A method of preparing the wound dressing material comprises the steps of:

[1] preparing the gelatin derivative, [2] spray drying or pulverizing the gelatin derivative in solid state after drying to form particles, and [3] heat treating. Each step will be explained below.

[1] Preparing the Gelatin Derivative (1) Preparation of an Aqueous Solution of an Original Gelatin A starting original gelatin is dissolved in water or an aqueous solvent at a concentration of from 5 to 50 wt/v % by heating at 40 to 90° C. Water may be ultrapure water, deionized water, or distilled water. As the aqueous solvent, a mixture of water and water soluble organic solvent is used. Examples of the water soluble organic solvent include alcohols having 1 to 3 carbon atoms and esters having 1 to 3 carbon atoms, and preferably ethanol is used.

(2) Derivatization

To the solution of the gelatin obtained in the step (1), a derivatizing agent having an alkyl group to be introduced to the gelatin is added and a mixture thus obtained is subjected to a reaction while stirring for a predetermined period of time. As the derivatizing agent, an aldehyde or a ketone having the alkyl group is used such as dodecanal, tetradecanal, and decyl ethyl ketone. A reaction temperature ranges from 30 to 80° C., and a reaction time ranges from 0.5 to 12 hours, Normally, a gelatin derivative having the alkyl group bonded to an amino group of the gelatin via a Schiff base (GltnN=$CR^1R^2$) can be obtained only by stirring. The aldehyde is used in an amount of from 1 to 4 times the stoichiometric amount corresponding to a desired derivatization ratio, preferably, 1 to 2 times.

Subsequently, the Schiff base is reduced to the structure of the above formula (1). A known reducing agent can be used such as sodium cyanoborohydride ($NaBH_3CN$), sodium triacetoxyborohydride ($NaBH(OAc)_3$), 2-picoline borane, and pyridine borane, among which 2-picoline borane is preferred. The picoline borane is stable to allow a one-pot reductive amination reaction of aldehydes or ketones in an aqueous solvent. In addition, a yield of from 80 to 90% can be achieved. Preferably, 2-picoline borane is used in an amount of from 1 to 3 equivalents relative to an equivalent of a derivatizing agent. It should be noted that the reducing agent and the aldehyde or the like can be added in any order and any one of them can be added to gelatin solution before the other, or they may be added simultaneously.

(3) Purification

To the reaction solution obtained in the step (2), a large excess amount of a poor solvent such as cold ethanol is added, or the reaction solution is added to cold ethanol to precipitate a gelatin derivative. After isolating the precipitate by filtration, it is washed with ethanol or the like to obtain a final product.

[2] Forming Particles

<Spray Drying>

It has been found that shape and particle size or the like depend on various variables such as gas flow velocity. In addition to the aforesaid molecular weight of the original gelatin, factors including gelatin derivative concentration, drying temperature, gas flow velocity, and solution flow velocity were examined to obtain as large particle as possible in the aforesaid range of particle size mainly from the viewpoint of handling property as wound dressing material. Each factor will be explained below.

A spray dryer may be of any type, for example, disc type, nozzle type, cyclone collection type, or filter collection type.

Spray drying is performed by spraying a solution of the gelatin derivative dissolved in a mixed solvent of water and a water miscible organic solvent in the presence of an inert gas such as nitrogen. Examples of the organic solvent include alcohols having 1 to 3 carbon atoms and esters having 1 to 3 carbon atoms, among which ethanol is preferably used. A mixing ratio in volume of water/the organic solvent ranges from 10/0 to 3/7, preferably from 6/4 to 4/6. In the method described in Patent Document 1, an aqueous solution of gelatin is used. However, for the gelatin derivative in the present invention, it is difficult for an aqueous solution thereof to form particles and to provide a satisfactory adhesion strength. As a result of extensive studies, particles having a superior adhesiveness can be obtained by using the aforesaid mixed solvent. It is considered, without intending to limit the present invention, that the use of the organic solvent increases an evaporation rate of the solvent whereby alkyl groups in the gelatin derivative are accumulated at a gas/liquid interface to appear on a surface of sphere.

The solution may be prepared by adding water to the gelatin derivative, then stirring at 50 to 90° C. to dissolve, and adding to thus obtained aqueous solution an organic solvent to make a concentration of the gelatin derivative ranging from 1 to 7 w/v %, preferably 3 to 5 w/v %. At a concentration below the aforesaid lower limit, it would be difficult to obtain particles, whereas at a concentration above the aforesaid upper limit a proportional increase of a yield would not be achieved because particles tend to stick to a glass wall of a spray dryer before reaching a collecting container.

A drying temperature ranges from 140 to 220° C., preferably from 160 to 200° C. At a temperature below the aforesaid lower limit, a particle size tends to be smaller than 1 μm, whereas at a temperature above the aforesaid upper limit particles tend to agglomerate.

A flow rate of the inert gas ranges from 400 to 500 L/h, preferably from 400 to 480 L/h. A flow rate of the gelatin derivative solution ranges from 300 to 500 mL/h, preferably from 350 to 450 mL/h.

<Mechanical Pulverization>

The purified gelatin derivative is dissolved in ultrapure water and then dried at 40 to 60° C. into a solid state, followed by pulverization with a pulverizer, for example, roller mill, jet mill, hammer mill or the like. In preparing the solution, a dispersion medium such as polyethylene glycol or the like may be added.

[3] Heat Treating

Particles obtained by spray drying or mechanical pulverization are heat treated to crosslink gelatin derivative. Temperature and time of heating should be appropriately adjusted according molecular weight of an original gelatin, degree of derivatization, and intended degree of crosslinking. An original gelatin having a molecular weight (Mw) of about 100,000 is heated at 140 to 160° C. for at least 3 hours.

After heat treating, particles may be subjected to cleaning, drying, and screening as well as treatments for supporting a drug thereon.

<Application to the Tissues>

Figure 2:
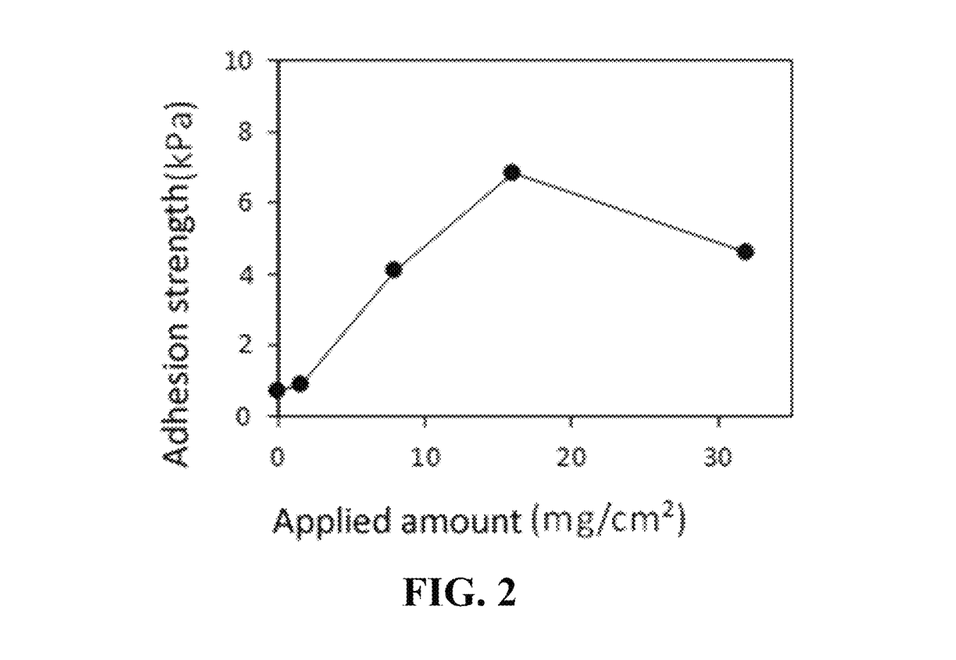
FIG. 2 is a graph showing a change in adhesion strength according to applied amount of the gelatin derivative particles.

The wound dressing material of the preset invention can be applied to incised parts in various surgeries, for example, respiratory surgery, especially wounds after lung cancer surgery, gastrointestinal surgery, cardiovascular surgery, oral surgery, and gastrointestinal medicine, and skin wounds. In ESD, it can be applied in the dry state using hemostatic forceps, stent, balloon, or endoscope. An amount of application thereof can be adjusted according to application site, and wound. In the viewpoint of adhesion strength, preferred amount per area of tissue was found in the range of from 10 to 20 mg/cm' based on adhesion strength measurements performed in the same manner as Examples described below by varying amount of from 1.6 to 32 g/cm$^2$ of particles applied to porcine stomach lining tissues (FIG. 2).

EXAMPLES

The present invention will be explained with reference to the Examples, but the present invention is not limited thereto.

<Preparation of Gelatin Derivatives>

Gelatin derivatives shown in Table 1 were prepared. Method of preparation thereof will be explained for gelatin derivative 7 as an example. A porcine skin-derived alkali-treated gelatin (Mw=100,000, beMatrix™, Nitta Gelatin Inc.) in an amount of 5 g was added to 50 mL of ultrapure water in an eggplant shaped flask placed in an oil bath at 50° C., and was dissolved into a 10 wt % aqueous solution while stirring. To the aqueous solution thus obtained, 777 mg of picoline borane (Junsei Co., corresponding to about 1.5 equivalents of octanal) dissolved in 5 mL of ethanol was added, and then octanal (Tokyo Chemical Industry Co., Ltd.) dissolved in 70 mL of ethanol was added by dropwise at a rate of about 100 mL/h to 621 mg in total, which amount corresponds to about 3 equivalents of stoichiometric amount of derivatization ratio of about 75 mol %. To the eggplant shaped flask, a reflux condenser was attached and the contents of the eggplant shaped flask were subjected to a reaction at 50° C. for 17 hours while stirring. After taking out the eggplant shaped flask from the oil bath, ethanol therein was removed at 40° C. by using an evaporator. The reaction solution thus obtained was dropped in 1 L of ethanol contained in a beaker placed in an ice bath to precipitate. After stirring for 1 hour, the beaker was left stand for 1 hour in a freezer and then filtered with a glass filter. The obtained filtration residue was subjected to reprecipitation by dropping in 1 L of ethanol contained in a beaker. After stirring for 1 hour, the beaker was left to stand for 1 hour in a freezer and then filtered with a glass filter. The filtration residue thus obtained was dried in a vacuum dryer for at least one overnight whereby the gelatin derivative having an octyl group was obtained with about 83% yield.

An introduction ratio of octyl group in the obtained gelatin derivative was determined by the following method. The original gelatin and the gelatin derivative were respectively dissolved in a mixed solvent of water/DMSO (volume ratio of 1/1, the same applies hereinafter) at a concentration of 0.1 w/v % and 100 μL of each solution thus obtained was dispensed in a 48-well plate. To each solution in the well, 100 μL of 0.1 v/v % trimethylamine (TEA, Nacalai Tesque, Inc.) solution dissolved in the mixed solvent of water/DMSO was added and stirred at 400 rpm for 1 minute by using a plate shaker. Then, 100 μL of 0.1 w/v % trinitrobenzene sulfonic acid (TNBS, FUJIFILM Wako Pure Chemical Co.) solution dissolved in the mixed solvent of water/DMSO was added and stirred at 400 rpm for 1 minutes by using the plate shaker. The wells were shielded from light with aluminum foil and, after left to stand in an incubator at 37° C. for 2 hours, the plate were taken out from the incubator, to which 504, of 6N HCl was added to stop the reaction and then stirred at 400 rpm for 1 minutes by using the plate shaker. The wells were shielded from light and, after left to stand for 10 minutes, light absorption (Abs) at 340 nm was measured with a spectrophotometer (Spark 10M-NMST, TECAN Co.). After subtracting the absorbance of the blank sample, which differs only in that it did not contain gelatin, the introduction ratio of octyl group was determined to be 75 mol % according to the following equation:

$$\text{An introduction ratio (\%)} = [\text{Abs(original gelatin)} - \text{Abs(gelatin derivative)}]/[\text{Abs(original gelatin)}] \times 100$$

Figure 3:
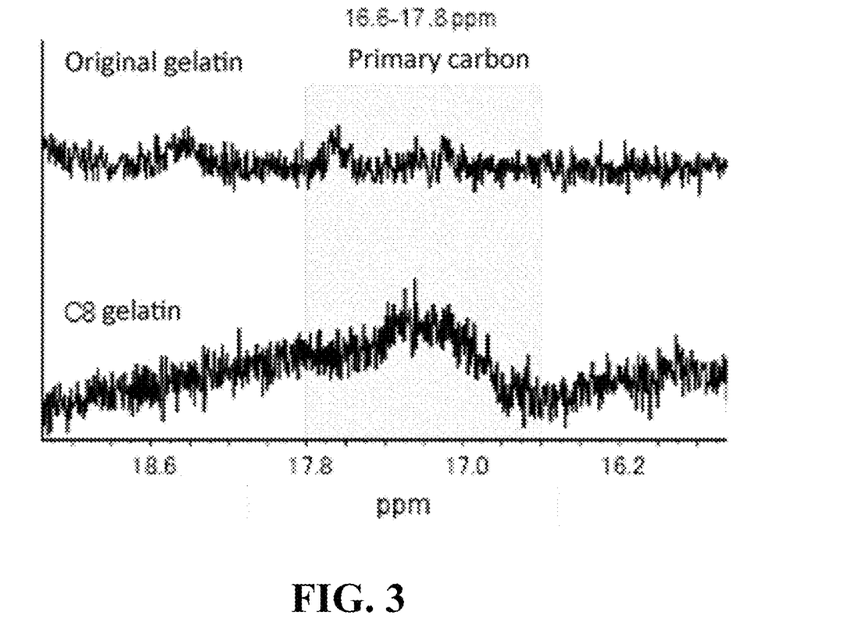
FIG. 3 shows a $^{13}$C-NMR spectrum of the gelatin derivative.

The gelatin derivative was analyzed by $^{13}$C-NMR and FT-IR. For $^{13}$C-NMR measurement, each gelatin derivative and the original gelatin was dissolved in heavy water (containing 3-(trimethylsilyl)-1-propanesulfonic acid sodium salt as the internal standard) at a concentration of 20 wt % and the measurement was performed at 50° C. FIG. 3 shows $^{13}$C-NMR spectra obtained. The gelatin derivative showed a peak around 17-17.5 ppm assigned to a primary carbon atom whereby it was confirmed that an octyl group had been introduced in the gelatin. FT-IR measurement was performed on the gelatin derivative powder placed on a sample table. FIG. 4 shows 2500 to 3500 cm$^{-1}$ region of FT-IR spectra. Peaks assigned to stretching vibration of methyl group (2868 cm$^{-1}$), stretching vibration of methylene group (2929 cm$^{-1}$), and N—H stretching (3299 cm$^{-1}$) were observed.

The other gelatin derivatives were prepared in the same manner as above except that, in place of octanal, ethanal, butanal, hexanal, and undecanal were used each in an amount according to an intended derivatization ratio. Yields thereof ranged from 80 to 90%. In Table 1 and so on, the expression, "75C8", for instance, represents a gelatin derivatized with C8 aldehyde (in the formula (1), $R^1$ is heptyl group and $R^2$ is hydrogen atom) at a derivatization ratio of 75 mol %.

TABLE 1

| Gelatin derivative | | Derivatization ratio |
|---|---|---|
| No. | Sample name | (mol %) |
| 1 | 30C2 | 30 |
| 2 | 72C4 | 72 |
| 3 | 67C6 | 67 |
| 4 | 13C8 | 13 |
| 5 | 29C8 | 29 |
| 6 | 63C8 | 63 |
| 7 | 75C8 | 75 |
| 8 | 41C12 | 41 |

Figure 5:
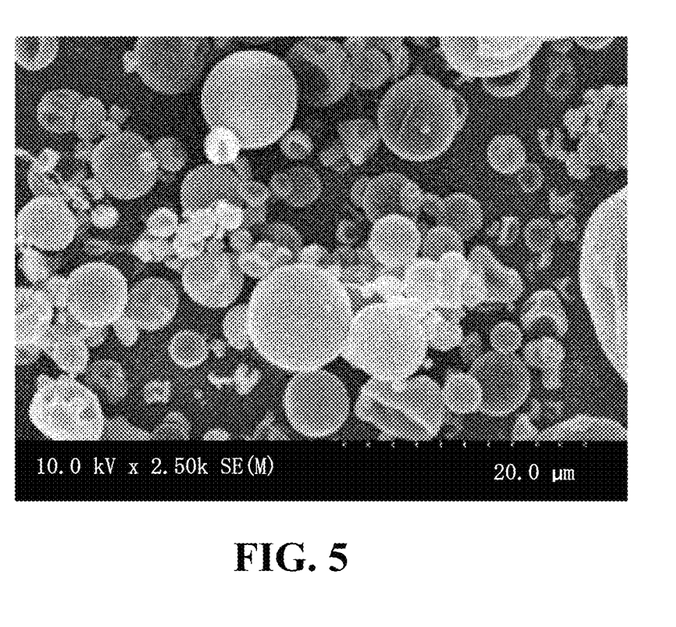
FIG. 5 shows a SEM image of spray dried particles of gelatin derivative before heat treatment.

<Spray Drying>
(1) The gelatin derivative was dissolved in ultrapure water at 50° C. to prepare 6 wt % aqueous solution.
(2) To the aqueous solution, the same volume of ethanol was added to prepare 3 wt % solution.
(3) A temperature of the solution was kept at 50° C. and the solution was set in a spray dryer (mini spray dryer, B-290, BÜCHI Labortechnik AG), and spray dried to form particles in the conditions of a temperature of 180° C., a nitrogen gas flow rate of 440 L/h, and a flow rate of the solution of 410 mL/h. FIG. 5 shows a SEM image of spray dried particles obtained from the gelatin derivative 7 before heat treatment. As a comparative example, the original gelatin not derivatized was also spray dried in the similar manner.

<Heat Treatment>
Based on the aforesaid studies on heat treatment with reference to FIGS. 6 and 7, particles were heat treated at 150° C. for 3 hours.

Gelatin derivatives 1-6, 8, and the original gelatin were spray dried and heat treated (150° C. for 3 hours) in the same manner to form particles.

FIG. 1 shows a SEM image of particles obtained from gelatin derivative 7. The particles were substantially spherical. Results of an image analysis showed that they has a size distribution of from about 1 μm to 1,000 μm, and a mode diameter of from 10 to 20 μm.

Figure 9:
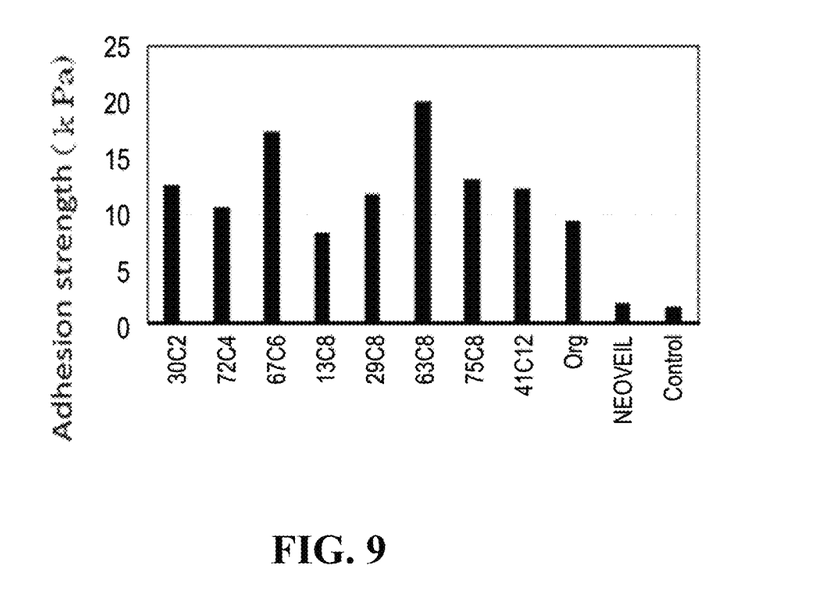
FIG. 9 is a graph showing adhesion strength of the gelatin derivative particles.

<Adhesion Strength Measurement of Particles to Porcine Stomach Lining Tissues>
Adhesion test was performed using porcine stomach lining tissues (Tokyo Shibaura Zouki Co., Ltd.). The test was performed according to the method of American Society for Testing and Materials (ASTM F-2258-05). A porcine stomach was opened, and mucosal layer thereof was removed. In this procedure, physiological saline was injected beneath the mucosal tissues and resulting uplifted parts were removed whereby only the mucosal layer was removed with submucosal tissues partly remaining. From the tissues thus obtained, 2.5 cm×2.5 cm pieces were cut out. One piece was fixed on an upper jig of the test instrument and another piece was on a lower jig with an instant adhesive. During the measurement, the porcine stomach lining tissues were kept at 37° C. by using a hot plate. After removing excess water on surfaces of the pieces by KimWipes™, 100 mg (16 mg/cm²) of the gelatin particles were placed on the lower piece. After pressing the particles with the upper jig at a pressure of 80 kPa for 3 minutes, an adhesion strength was measured by pulling up the upper jig. The particles obtained from the original gelatin was used as Comparative Example 1, NEOVEIL (trademark) was used as Comparative Example 2, and "Control" is a blank value with no sample. Results are shown in Table 2 and FIG. 9.

TABLE 2

| | | Adhesion strength (kPa) |
|---|---|---|
| | Sample name | Average (n = 5) |
| Example 1 | 30C2 | 12.5 |
| Example 2 | 72C4 | 10.5 |
| Example 3 | 67C6 | 17.5 |
| Example 4 | 13C8 | 8.3 |
| Example 5 | 29C8 | 11.7 |
| Example 6 | 63C8 | 20.1 |
| Example 7 | 75C8 | 13.1 |
| Example 8 | 41C12 | 12.2 |
| Comparative Example 1 | Org | 9.3 |
| Comparative Example 2 | NEOVEIL | 1.9 |
| | Control | 1.6 |

<Hemostatic Effect>
In a 5-mL vial, 1 mL of whole blood taken from a rat (6-week-old female Wister rat) was placed. To the vial, 50 mg of particles of Example 7 (75C8) were added, mixed lightly and left to stand. As a control, the whole blood without any additive was used. At 3 minutes after mixing, the blood sample containing 75C8 particles clotted whereas the control sample did not. This indicates that the gelatin derivative particles of the present invention have a hemostatic effect.

<Evaluation of Hydrophobicity of Gelatin Derivative Particles by Contact Angle Measurement>
Pellets were prepared by placing 100 mg of each particles of Example 1 (C2), Example 2 (C4), Example 3 (C6), Example 6 (C8), Example 8 (C12) and Comparative Example 1 (ORG) on a slide glass, sandwiching the particles with another slide glass, and then manually pressing the particles. Using a contact angle meter (DM-700, Kyowa Interface Science Co., Ltd.), a drop of ultrapure water was dropped on a surface of the pellet. At 200 seconds later, an angle between the drop and the surface of the pellet was measured. Results are shown in FIG. 10.

Figure 10:
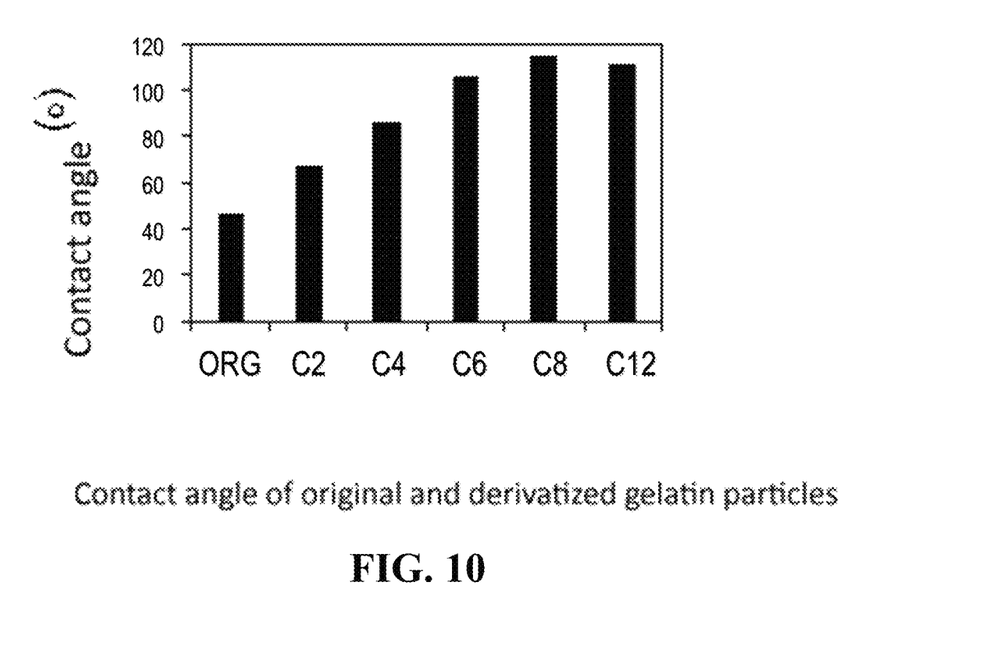
FIG. 10 is a graph showing contact angles to water of gelatin (without modification) and gelatin derivative (hydrophobically modified gelatin).

As shown in FIG. 10, Comparative Example 1 showed a contact angle of 46 degrees, indicating hydrophilic surface, whereas the particles of Examples showed increasing contact angles with increasing alkyl chain length of modifier. In particular, from C6 to C12, hydrophobic surfaces were observed with a contact angle exceeding 100 degrees. It was thus found that particles having a higher hydrophobic surface can be produced by modifying gelatin with a group having a higher hydrophobicity.

<Evaluation of Cell Survival Rate>
Using RAW264 cells, which are macrophage-like cells derived from mouse, influences of the gelatin derivative particles on survival rate of the cells were evaluated. RAW264 cells were seeded at a concentration of $6\times10^4$ cells/cm² in a 96-well plate and cultured in RPMI1640 medium (10% fetal bovine serum, 1% non-essential amino acid, 1% antibiotic) at 37° C. in a 5% $CO_2$ incubator for 24 hours. To the cells, 100 μ, of a dispersion of particles of Example 1 (C2), Example 2 (C4), Example 3 (C6), Example 6 (C8), Example 8 (C12) and Comparative Example 1 (ORG) each dispersed in the above medium at concentrations of 0.625, 1.25, 2.5, 5, or 10 mg/mL was added. After culturing for 24 hours, the cells were counted using a cell counting kit (WST-8, Dojindo Laboratories). The number of cells of each sample are shown in the graph (FIG. 11) with the number of cells in the well without particles being 100%.

Figure 11:
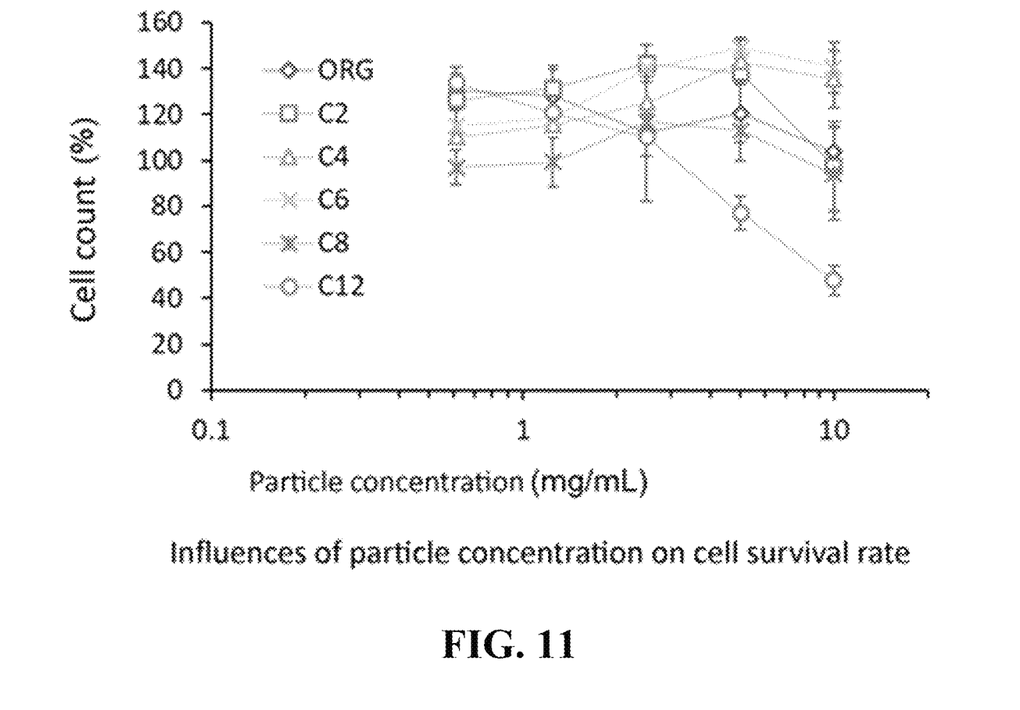
FIG. 11 is a graph showing survival rates of RAW264 cell in the presence of gelatin derivative particles.

The samples containing particles of Example 1 (C2), Example 2 (C4), Example 3 (C6), Example 6 (C8), or Comparative Example 1 (ORG) showed a large number of cells, whereby a high cell compatibility was confirmed. Particles of Example 8 (C12), on the other hand, showed a decrease in cell number at a concentration of 2.5 mg/mL or higher. It follows that it would be preferred for particles having a long alkyl chain to be applied to a wound at a relatively low concentration.

<Influences of Gelatin Derivative Particle on Cell Growth>

Wound healing involves an epithelialization process where new epithelial cells grow to close the wound. To evaluate influences of gelatin derivative particles on cell growth, growth behaviors of Caco-2 cells derived from human epithelial colorectal adenocarcinoma cells on film made of the gelatin particles were evaluated. To a 96-well plate, 1004, of a dispersion of particles of Example 1 (C2), Example 2 (C4), Example 3 (C6), Example 6 (C8), Example 8 (C12) and Comparative Example 1 (ORG) each dispersed in ultrapure water at a concentration of 0.2 mg/mL was added. By evaporating ultrapure water, films composed of the particles were prepared. After sterilizing the films by 1-hour UV radiation, Caco-2 cells were seeded on the films at a concentration of $6 \times 10^3$ cells/cm$^2$ and then cultured in DMEM medium (20% fetal bovine serum, 1% non-essential amino acid, 1% antibiotic) at 37° C. in a 5% $CO_2$ incubator. After culturing for 24 hours, the cells were counted using a cell counting kit (WST-8, Dojindo Laboratories). Results are shown in FIG. 12.

Figure 12:
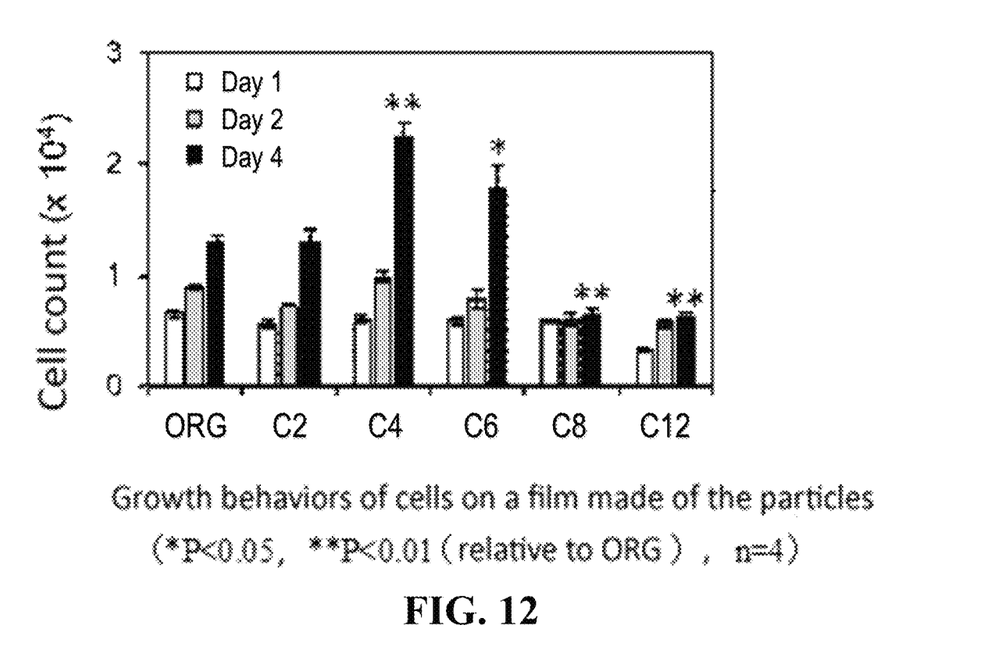
FIG. 12 is a graph showing growth behaviors of Caco-2 cells on a film made of gelatin derivative particles.

As can be found from FIG. 12, the cells grew on the films of Example 1 (C2), Example 2 (C4), Example 3 (C6), and Comparative Example 1 (ORG) and, in particular, particles of Example 2 (C4), Example 3 (C6) showed significantly higher growth property than Comparative Example 1, implying capability of promoting epithelialization process. On the other hand, on the films of Example 6 (C8), and Example 8 (C12), the growth of Caco-2 cells were suppressed. This may possibly be caused by alkyl chain density on the films, considering the aforesaid results of cell survival rate.

<Influences on Cytokine Production of Gelatin Derivative Particles>

Figure 13:
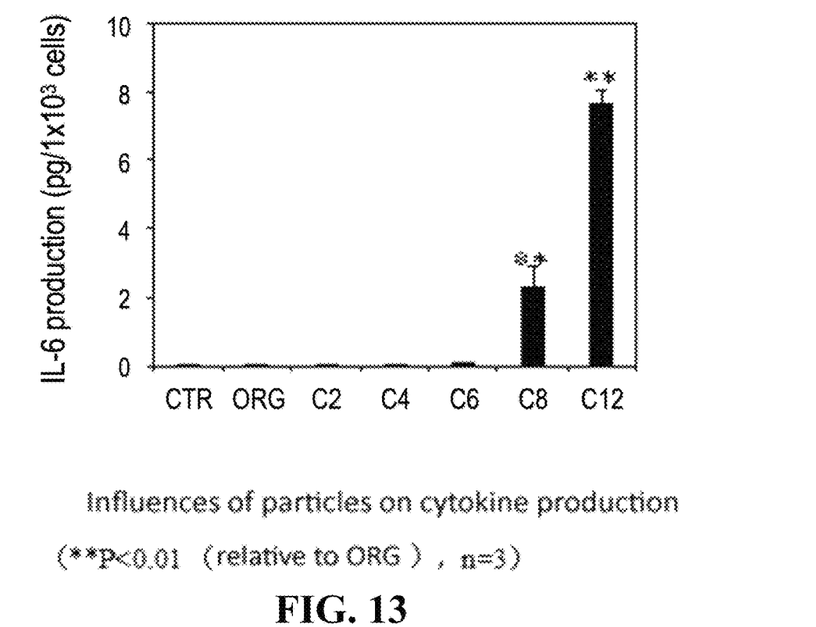
FIG. 13 is a graph showing amounts of IL-6 produced by RAW264 cells in the presence of gelatin derivative particles.

Mouse IL-6 assay was performed in the same manner as in the evaluation of cell survival rate except that mouse IL-6 was quantified in a supernatant collected after 24-hour culture by using ELISA assay kit (R&D systems, Inc.) instead of counting cells. Results are shown in FIG. 13. In the figure, "CTR" means a sample with no particle. As shown in FIG. 13, IL-6 was produced in the presence of the particles of Example 6 (C8), and Example 8 (C12), and especially more IL-6 was produced in the presence of the particles of Example 8 (C12). IL-6 is involved in fever development and angiogenesis in an acute phase response involved in a recovery from an undesired inflammatory state and has various physiological activities. It is expected that the use of the particles of Example 6 (C8), or Example 8 (C12) promote wound healing.

<Effects of Wound Healing>

To evaluate effects of promoting wound healing of the particles of the present invention, experiments on rats were performed. Under inhalation anesthetic using isoflurane, a full-thickness skin defect model on the back of a rat (7-week old female) was made using 8-mm DarmaPunch™. To the defect, 10 mg of particles of Example 2 (C4), Example 3 (C6), Example 6 (C8), Example 8 (C12) and Comparative Example 1 (ORG) were each applied. As Control (CTR), a sample without particles applied thereon was used. The samples were covered with a silicone sheet, which was fixed by an adhesive tape, whereby the samples were kept stable. The wounds were photographed (FIG. 14, upper row) and areas thereof were measured (FIG. 14, lower row) on 7 days and 14 days later, respectively, and tissue sections thereof were observed (FIG. 15) on 7 days later.

Figure 14:
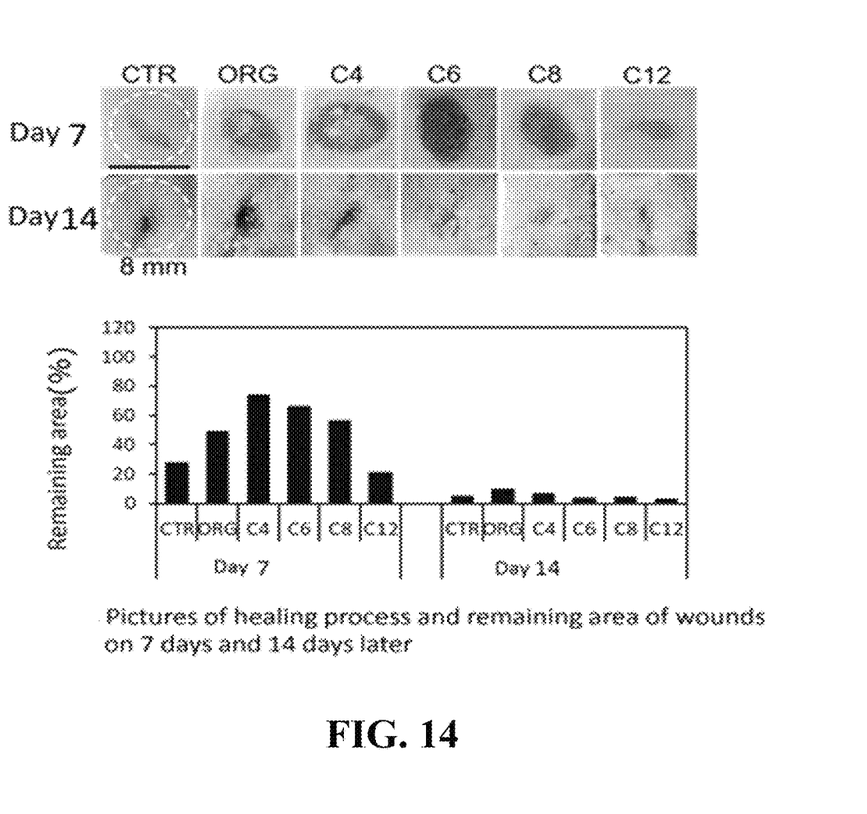
FIG. 14 shows photographs (upper row) of healing process of wounds in rat skin on which gelatin derivative particles were applied and a graph of areas of remaining wound (lower row).
Figure 15:
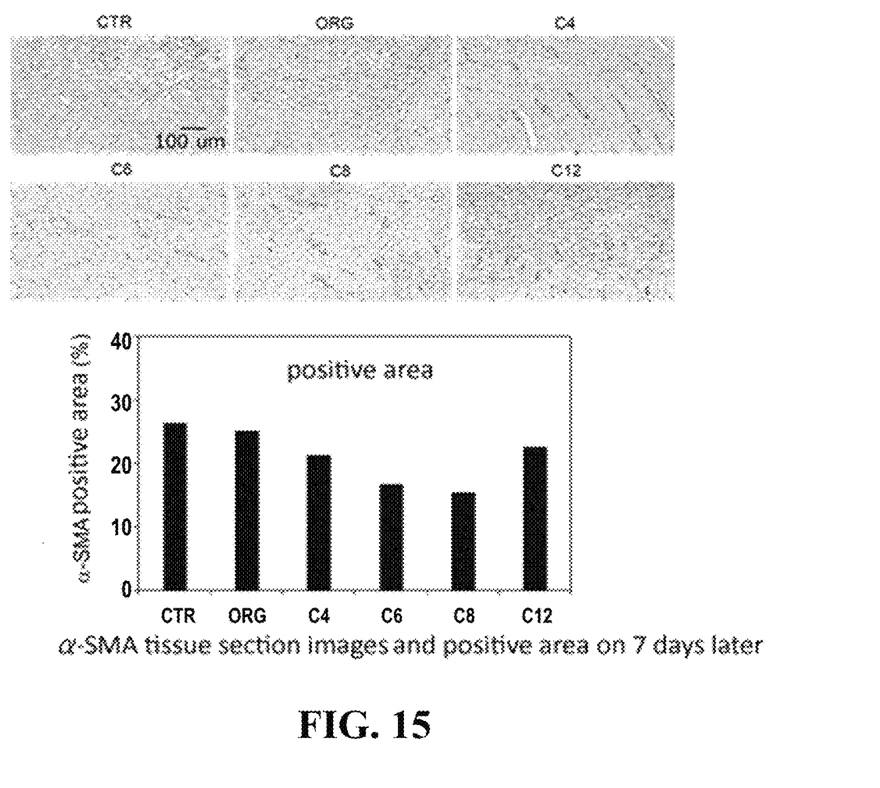
FIG. 15 shows photographs of α-smooth muscle actin positive parts (upper row) and a graph of positive area of tissues (lower row) observed on 7 days after the application of gelatin derivative particles to wounds in rat skin.

As shown in FIG. 14, on 7 days later, Examples showed significantly larger remaining wound areas except that Example 8(C12) showed almost the same degree of wound closure as that in CTR. In wound healing process, if a wound is closed rapidly before an inflammatory response subsides, scar contracture occurs, which possibly causes constriction. Accordingly, a larger remaining wound area is preferable. The larger remaining wound area indicated that scar contracture is suppressed by applying the particles of the present invention. On 14 days later, all the samples showed closure of the wound.

By observing the tissue sections on 7 days later, a level of inflammation was evaluated. The rats were sacrificed by using an excess amount of Somnopentyl (tradename) and the tissues of the wound were collected. After embedding the tissues in paraffin, thinly sliced samples were prepared, and α-smooth muscle actin (α-SMA), which is a protein expressed by inflammation, was stained and observed. A quantitative analysis of α-SMA-positive area was performed by using an image processing software, ImageJ (tradename). As is found from the graph shown in the lower row in FIG. 15, the particles of all the Examples, including those of Example 8 (C12), which showed almost the same level of wound closure as that of CTR, suppressed expression of α-SMA more than CTR. From these results, it is expected that the use of the particles of the present invention as wound dressing material can suppress inflammation and promote healing of wounds.

<Preparation of Particles by Mechanical Pulverization>

Figure 16:
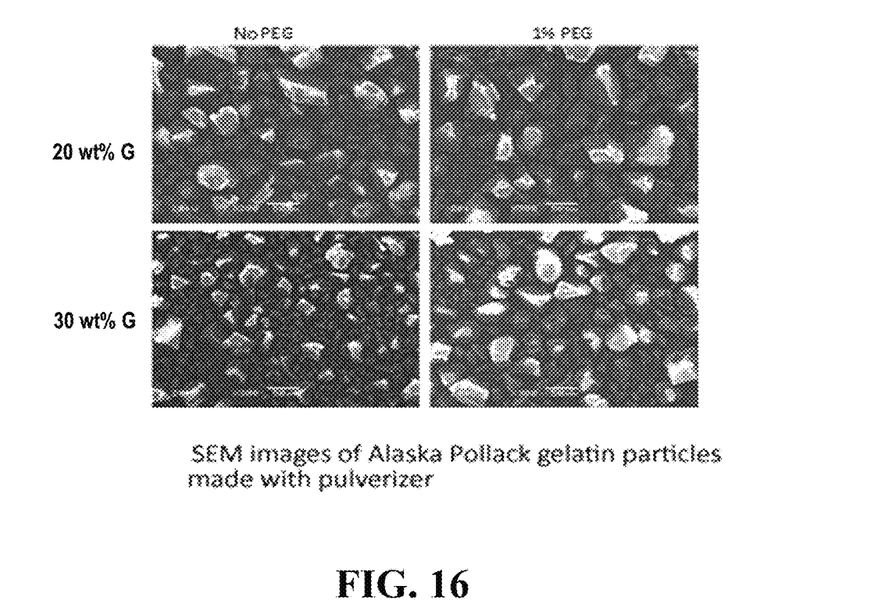
FIG. 16 shows SEM images of particles made by using Alaska Pollock gelatin and by mechanically pulverization.

Gelatin derivative was prepared in the same manner as Examples 1 to 8 except that an alkali-treated Alaska pollock gelatin (Mw=30 kDa, Nitta Gelatin Inc., hereinafter referred to as "Alaska pollock gelatin") in place of porcine skin-derived alkali-treated gelatin was used, and that about 2 equivalents of octanal was used. A ratio of derivatization was 58 mol % (58C8). The gelatin derivative thus obtained was dissolved in ultrapure water to prepare 20 wt % and 30 wt % solutions, which were placed in a TEFLON' tray and heated at 40° C. to dry, whereby gelatin derivative in a solid state was obtained. To evaluate effects of the presence of a dispersion medium, a sample was prepared where 1% polyethylene glycol (PEG, Mw=1500 Da) was added before drying. The solid gelatin derivatives after drying were pulverized for 1 minute for 3 times by using a pulverizing mill (Wonder Crusher). Finally, 3-hour heat treatment at 150° C. for thermal crosslinking was performed. The particles thus obtained had a particle size of from 20 to 50 μm as shown in SEM images (FIG. 16). There was no significant difference in particle size between the particles with and those without using PEG.

Figure 17:
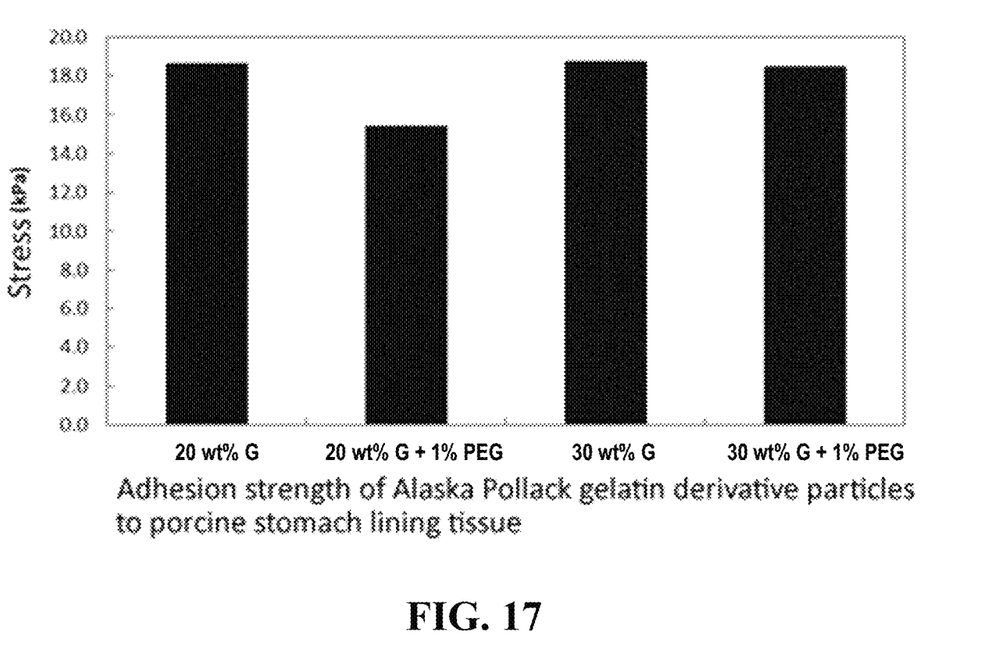
FIG. 17 is a graph showing adhesion strength of Alaska Pollock gelatin particles prepared by mechanical pulverization.

An adhesion strength to porcine stomach lining tissues was measured as in Example 1 or the like. Results are shown in FIG. 17. From the results of the adhesion test, Alaska pollock gelatin was found to have an adhesion strength equivalent to that of porcine gelatin (15 to 20 kPa). Further, it was found that particles having an excellent adhesion strength can be obtained by drying and pulverizing without using a dispersion medium.

INDUSTRIAL APPLICABILITY

The wound dressing material of the present invention is very useful for applying to wounds and vascular anastomotic portions or the like in surgeries such as endoscopic submucosal dissection.

What is claimed is:

1. A wound dressing material comprising a particle comprising a thermally crosslinked gelatin derivative, the gelatin derivative comprising the structure represented by the following formula (1):

$$GltnNH\text{—}CHR^1R^2 \tag{1}$$

wherein "Gltn" represents a gelatin residue, $R^1$ represents an alkyl group having 1-17 carbon atoms, and $R^2$ represents a hydrogen atom or an alkyl group having 1-17 carbon atoms, and the particle having a particle size ranging from 1 to 1,000 μm.

2. A method for preparing the wound dressing material according to claim 1, comprising:
preparing the gelatin derivative comprising the structure represented by the aforesaid formula (1);
spray drying a solution of the gelatin derivative or pulverizing the gelatin derivative in solid state to form particles; and
heat treating the formed particles by heating at a temperature of from 140 to 160° C. for at least 3 hours.

3. The wound dressing material according to claim 1, wherein the gelatin is an alkali-treated gelatin derived from porcine gelatin or Alaska pollock gelatin.

4. The wound dressing material according to claim 3, wherein the gelatin derivative has a molar ratio of imino group/amino group ranging from 20/80 to 80/20.

5. A method for preparing the wound dressing material according to claim 3, comprising:
preparing the gelatin derivative comprising the structure represented by the aforesaid formula (1);
spray drying a solution of the gelatin derivative or pulverizing the gelatin derivative in solid state to form particles; and
heat treating the formed particles by heating at a temperature of from 140 to 160° C. for at least 3 hours.

6. The wound dressing material according to claim 3, wherein the gelatin is a gelatin containing not more than 10 EU/g endotoxin.

7. The wound dressing material according to claim 6, wherein the gelatin derivative has a molar ratio of imino group/amino group ranging from 20/80 to 80/20.

8. A method for preparing the wound dressing material according to claim 6, comprising:
preparing the gelatin derivative comprising the structure represented by the aforesaid formula (1);
spray drying a solution of the gelatin derivative or pulverizing the gelatin derivative in solid state to form particles; and
heat treating the formed particles by heating at a temperature of from 140 to 160° C. for at least 3 hours.

9. The wound dressing material according to claim 1, wherein the gelatin derivative has a molar ratio of imino group/amino group ranging from 20/80 to 80/20.

10. A method for preparing the wound dressing material according to claim 9, comprising:
preparing the gelatin derivative comprising the structure represented by the aforesaid formula (1);
spray drying a solution of the gelatin derivative or pulverizing the gelatin derivative in solid state to form particles; and
heat treating the formed particles by heating at a temperature of from 140 to 160° C. for at least 3 hours.

* * * * *